(12) United States Patent
Tamersoy et al.

(10) Patent No.: US 11,837,352 B2
(45) Date of Patent: Dec. 5, 2023

(54) BODY REPRESENTATIONS

(71) Applicant: Siemens Healthcare GmbH, Erlangen (DE)

(72) Inventors: Birgi Tamersoy, Erlangen (DE); Ankur Kapoor, Plainsboro, NJ (US); Vivek Singh, Princeton, NJ (US); Brian Teixeira, Lawrence Township, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 373 days.

(21) Appl. No.: 17/231,041

(22) Filed: Apr. 15, 2021

(65) Prior Publication Data
US 2021/0358595 A1 Nov. 18, 2021

(30) Foreign Application Priority Data
May 12, 2020 (EP) .................................... 20174249

(51) Int. Cl.
*G16H 30/20* (2018.01)
*G06N 20/00* (2019.01)

(52) U.S. Cl.
CPC ............. *G16H 30/20* (2018.01); *G06N 20/00* (2019.01)

(58) Field of Classification Search
CPC ................................ G16H 30/20; G06N 20/00
See application file for complete search history.

(56) References Cited

U.S. PATENT DOCUMENTS

| 2013/0177230 A1* | 7/2013 | Feng .................... G06T 7/75 |
| | | 382/132 |
| 2018/0260997 A1* | 9/2018 | Petkov ................ G06F 18/214 |
| 2020/0161005 A1* | 5/2020 | Lyman .................. G16H 10/20 |
| 2020/0210767 A1* | 7/2020 | Do ...................... G06T 11/008 |

(Continued)

FOREIGN PATENT DOCUMENTS

EP 3483895 A1 * 5/2019 ........... G06T 11/008

OTHER PUBLICATIONS

G. Riegler, M. Urschler, M. Rüther, H. Bischof and D. Stern, "Anatomical Landmark Detection in Medical Applications Driven by Synthetic Data," 2015 IEEE International Conference on Computer Vision Workshop (ICCVW), Santiago, Chile, 2015, pp. 85-89, doi: 10.1109/ICCVW.2015.21. (Year: 2015).*

(Continued)

*Primary Examiner* — Sun M Li

(57) ABSTRACT

For training a machine learning system for representing a patient body a plurality of stored medical imaging data sets each representing at least a part of a respective patient are obtained. A first one of the plurality of stored medical imaging data sets represents a different part of the patient body than a second one of the plurality of stored medical imaging data sets. A plurality of landmarks in the stored medical imaging data sets are estimated, and each of the stored medical imaging data sets are aligned to a predefined pose using the plurality of landmarks. A plurality of points in the aligned medical imaging data sets are sampled, and the machine learning system is trained based on at least the plurality of points. The learned parameters of the machine learning system are then stored and used in a method for inferring a body representation.

19 Claims, 5 Drawing Sheets

(56) References Cited

U.S. PATENT DOCUMENTS

2021/0049756 A1* 2/2021 He .................... G06N 3/04
2021/0217164 A1* 7/2021 Weese ................ G06V 20/64

OTHER PUBLICATIONS

How Much Data is Needed to Train a Medical Image Deep Learning System to Achieve Neces-Sary High Accuracy ? Junghwan Cho, Kyewook Lee, Ellie Shin, Garry Choy, and †Synho Do * as:arXiv:1511.06348 [cs.LG] (or arXiv:1511.06348v2 [cs.LG] for this version) https://doi.org/10.48550/arXiv.1511.06348 (2016) (Year: 2016).*

A. Bannach et al., "Visual analytics for radiomics: Combining medical imaging with patient data for clinical research," 2017 IEEE Workshop on Visual Analytics in Healthcare (VAHC), Phoenix, AZ, USA, 2017, pp. 84-91, doi: 10.1109/VAHC.2017.8387545. (Year: 2017).*

S. Dua, V. Jain and H. W. Thompson, "Patient classification using association mining of clinical images," 2008 5th IEEE International Symposium on Biomedical Imaging: From Nano to Macro, Paris, France, 2008, pp. 253-256, doi: 10.1109/ISBI.2008.4540980. (Year: 2008).*

R. Koli, R. Pal, N. chaube, K. Joshi and A. Maithani, "Agile Data Mining Approach for Medical Image Mining," 2019 International Conference on Automation, Computational and Technology Management (ICACTM), London, UK, 2019, pp. 246-251, doi: 10.1109/ICACTM.2019.8776770. (Year: 2019).*

J. Liu and J. K. Udupa, "Oriented Active Shape Models," in IEEE Transactions on Medical Imaging, vol. 28, No. 4, pp. 571-584, Apr. 2009, doi: 10.1109/TMI.2008.2007820. (Year: 2008).*

Park, Jeong Joon et al: "DeepSDF: Learning Continuous Signed Distance Functions for Shape Representation", arxiv.org, Cornell University Library, XP081002960.

Mescheder, Lars, et al. "Occupancy networks: Learning 3d reconstruction in function space." Proceedings of the IEEE/CVF Conference on Computer Vision and Pattern Recognition. 2019.

Chen, Zhiqin, and Hao Zhang. "Learning implicit fields for generative shape modeling." Proceedings of the IEEE/CVF Conference on Computer Vision and Pattern Recognition. 2019.

Xue, et al., "Shape-Aware Organ Segmentation by Predicting Signed Distance Maps", arxiv.org, Cornell University Library, XP081547776.

* cited by examiner

BODY REPRESENTATIONS

RELATED APPLICATION

This application claims the benefit of EP 20174249.1 filed May 12, 2020, which is hereby incorporated by reference in its entirety.

TECHNICAL FIELD

The present embodiments relate to processing medical image data to determine a body representation, in particular, to improve the accuracy of such representations.

BACKGROUND

Medical imaging techniques may be used to obtain information regarding a human or animal body. For example, an X-ray image can be used to detect and classify bone fractures. In another example, Magnetic Resonance Imaging (MRI), computed tomography (CT), and ultrasound imaging can be used to image tissues of the body and monitor changes over time.

Image data captured by each of these modalities can be used to detect abnormalities in bone and/or tissues and enables snapshots to be taken at a given time. These snapshots can be analyzed to locate and classify the abnormalities. In some examples, it may be desirable to accurately target the imaging. This is particularly important where the imaging modality involves exposing a patient to radiation to capture the image data. In such examples, it is desirable to optimize the amount of radiation each patient is subjected to in order to provide the desired image quality. This may be achieved by determining an accurate body representation as well as for other purposes such as estimating a patient's weight, or the volume of organs or bones.

Accordingly, in some imaging modalities, the radiation can be targeted to the desired area using a representation of the human body.

It is an object to address at least some of the difficulties with providing accurate body representations.

SUMMARY

According to a first aspect, there is provided a computer-implemented method for training a machine learning system for representing a patient body, including obtaining a plurality stored medical imaging data sets each representing at least a part of a respective patient wherein a first one of the plurality of stored medical imaging data sets represents a different part of a patient body than a second one of the plurality of stored medical imaging data sets, estimating a plurality of landmarks in the stored medical imaging data sets, aligning each of the stored medical imaging data sets to a predefined pose using the plurality of landmarks to generate an aligned medical imaging data set, sampling a plurality of points in the aligned medical imaging data set, training the machine learning system based on the plurality of points to configure parameters of the machine learning system, and storing at least the parameters of the machine learning system.

Training a machine learning system for representing a patient body, based on aligned medical imaging data enables quick and efficient determination of a patient's body shape and size based on existing medical imaging data sources. This enables a representation of the patient's body to be estimated, which allows for accurate imaging of a patient. In some examples where the imaging modality involves exposing a patient to potentially harmful radiation, the accurate targeting of the radiation quanta required to undertake the imaging reduces the overall exposure of the patient to the radiation. It will be appreciated that other uses may be evident, some of which are described below.

Preferably, the stored medical imaging data set is at least one of computed tomography data, magnetic resonance imaging data, x-ray imaging data, and ultrasound imaging data. This enables the machine learning system to be trained using different types of imaging data since each imaging apparatus may require a patient to be positioned differently when imaging them.

Preferably, sampling a plurality of points includes for each of the plurality of points, determining a distance to a closest surface represented in the medical imaging data set. This enables information relating to the point to be determined and used for assessing the veracity of an output of a neural network.

Training the machine learning system includes adjusting at least one body representation, based on at least one of the plurality of points and corresponding distance to the closest surface. This enables multiple points to be assessed and the machine learning systems to adjust a body representation.

The at least one body representation may be an n-dimensional vector. This enables information regarding the body representation adjusted as part of the training process of the machine learning system to be stored efficiently for analysis by one or more algorithms.

Optionally, estimating a plurality of landmarks includes applying at least one landmark detection algorithm to the stored medical imaging data set. This enables efficient processing of the medical imaging data set to obtain landmark locations based on previously analyzed medical imaging data set.

Each landmark detection algorithm may be a machine learning algorithm trained to identify one or more landmarks of a human body. This enables the use of different landmarks to be identified using different algorithms specialized for detecting each specific landmark, thereby increasing efficiency.

The landmark may be a three-dimensional anatomical landmark. The use of three-dimensional anatomical landmarks enables more accurate positioning and orienting of the medical imaging data to the predefined pose.

Optionally, aligning the stored medical imaging data set, includes identifying at least one first medical data landmark in a first medical imaging data set, identifying at least one second medical data landmark in a second medical imaging data set, wherein the first medical data landmark and the second medical data landmark represent corresponding landmarks, and aligning the first medical imaging data set and the second medical imaging data set based on the first medical data landmark and the second medical data landmark. This enables multiple sets of the medical imaging data set, sometimes representing different portions of a patient body to be aligned before combining and aligning to the predefined pose providing additional detail for use during the training process.

The machine learning system (440) includes at least one neural network. This enables the training of the neural network based on the plurality of points and measured distances to optimize the network and body representations.

According to a second aspect, there is provided a computer-implemented method of inferring a human body representation, the method including receiving image data captured using an imaging modality, estimating a plurality of landmarks in the image data representing at least a part of a patient, aligning the image data to a predefined pose using the plurality of landmarks to generate aligned image data, sampling a plurality of points in the aligned image data, analyzing the plurality of points using a trained machine learning system, the machine learning system being configured to represent a patient body, inferring the human body representation based on the analysis, and outputting the inferred human body representation.

Inferring a body representation based on the trained machine learning system enables an accurate representation of the body to be inferred, thereby enabling accurate imaging of a patient. In some examples where the imaging modality involves exposing a patient to potentially harmful radiation. The accurate targeting of the radiation quanta required to undertake the imaging reduces the overall exposure of the patient to the radiation. It will be appreciated that other uses may be evident, some of which are described below.

Optionally, the image data is captured by an imaging apparatus, the image data being at least one of computed tomography data, magnetic resonance imaging data, x-ray imaging data, ultrasound data; point cloud data; and depth data. This enables body representations to be inferred for different types of image data since each imaging apparatus may require a patient to be positioned differently when imaging them.

Sampling a plurality of points may include, for each of the plurality of points, determining a distance to a closest surface represented in the image data, thereby determining a plurality of distances. This enables information relating to the point to be determined and used for assessing the veracity of an output of a neural network.

Preferably, inferring the body representation includes iteratively providing a body representation and a plurality of points to a trained machine learning system, and comparing the respective outputs of the machine learning system with the plurality of distances associated with the plurality of points. This enables the output of the machine learning system to be verified based on the plurality of points and an associated distance measured based on the image data according to the body representation provided.

Optionally, the method may further include adjusting the body representation based on the comparison between the respective outputs and the plurality of distances associated with the plurality of points. This enables adjustments to be made to the body representation based on the output of the machine learning system to determine whether a more accurate body representation is available based on the plurality of points and corresponding measured distances.

The body representation may be an n-dimensional vector. This enables information regarding the body representation to be stored efficiently for analysis by one or more algorithms.

Preferably, estimating a plurality of landmarks includes applying at least one landmark detection algorithm to the image data. This enables efficient processing of the image data to obtain landmark locations based on previously analyzed medical imaging data.

Each landmark detection algorithm may be a machine learning algorithm trained to identify one or more landmarks of a human body. This enables the use of different landmarks to be identified using different algorithms specialized for detecting each specific landmark, thereby increasing efficiency.

The landmark may be a three-dimensional anatomical landmark. The use of three-dimensional anatomical landmarks enables more accurate positioning and orienting of the medical imaging data to the predefined pose.

Optionally, aligning the image data includes identifying at least one first data landmark in the received image data, identifying at least one second data landmark data associated with the predefined pose, wherein the first data landmark and the second data landmark represent corresponding landmarks, and aligning the first image data and the predefined pose based on the first data landmark and the second data landmark. This enables multiple sets of the image data to be aligned before combining and aligning to the predefined pose providing additional detail when inferring body representation.

Preferably, the machine learning system is trained according to the first aspect.

According to a third aspect, there is provided an apparatus for inferring a body representation, the system including a training interface configured to obtain stored medical imaging data, a training unit (image processor or computer), configured to train at least one machine learning system based on the stored medical imaging data, an inference interface configured to receive image data captured using an imaging modality, and an inference unit (image processor or computer) configured to infer a body representation based on at least the captured image data using the trained machine learning system.

Inferring a body representation based on the trained machine learning system enables an accurate representation of the body to be inferred, thereby enabling accurate imaging of a patient. In some examples where the imaging modality involves exposing a patient to potentially harmful radiation. The accurate targeting of the radiation quanta required to undertake the imaging reduces the overall exposure of the patient to the radiation. It will be appreciated that other uses may be evident, some of which are described below.

According to a fourth aspect, there is provided a system for inferring a body representation, the system including an imaging apparatus configured to capture image data, storage for storing medical imaging data sets; and at least one processor arranged to undertake the method described above in relation to the first and/or second aspects, and arranged to obtain stored medical imaging data sets from the storage, and image data captured by the imaging apparatus.

According to a fifth aspect, there is provided a non-transitory computer-readable storage medium including a set of computer-readable instructions stored thereon which, when executed by at least one processor, cause the processor to carry out the method described above in relation to the first and/or second aspects.

BRIEF DESCRIPTION OF THE DRAWINGS

The above-mentioned attributes, features and advantages of this invention and the manner of achieving them will become more apparent and understandable with the following description of embodiments of the invention with reference to the accompanying drawings in which like reference numerals are used to denote like features.

DETAILED DESCRIPTION

Figure 1:
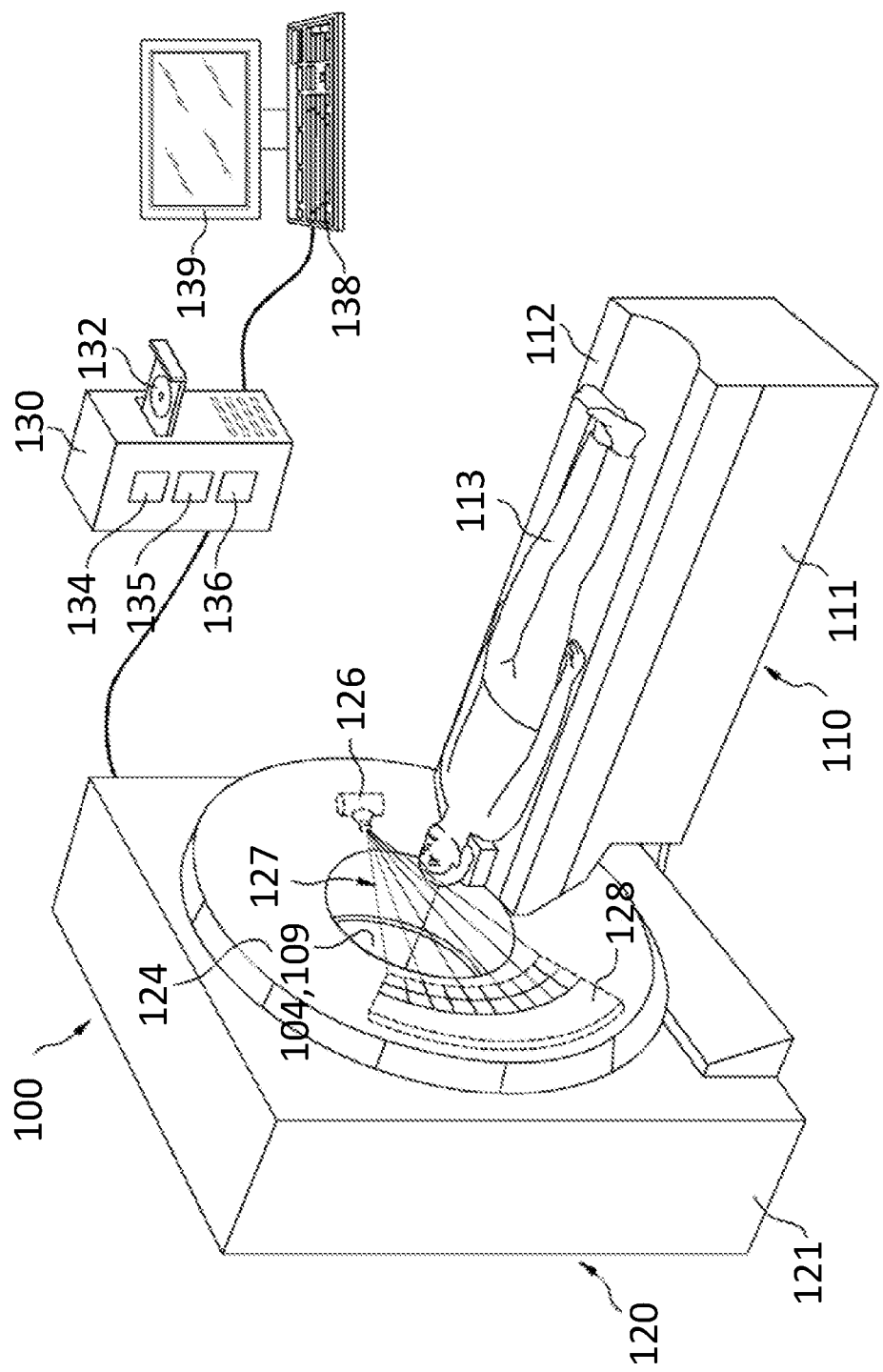
FIG. 1 is a schematic representation of a medical imaging device 1 according to an example.

FIG. 1 shows a medical imaging device 100 according to one aspect, including a data processing unit (data processor) 135.

A computed tomography device is shown, by way of example, for the medical imaging device 100, without limiting the general inventive idea.

The imaging device 100 has a gantry 120. The gantry 120 has a stationary support frame 121. The gantry 20 has a rotor 124 mounted so it can be rotated by a pivot bearing device. The imaging device 100 has an image recording region 104 formed by a tunnel-like opening 109. A region of an object to be imaged can be arranged in the image recording region 104.

The imaging device 100 has a patient-positioning device 110. The patient-positioning device 110 has a positioning table 111 and a transfer plate 112 for positioning the patient 113. The transfer plate 112 is arranged on the positioning table 111 so it can be moved relative to the positioning table 111 such that the transfer plate 112 can be introduced into the image recording region 104 in a longitudinal direction of the transfer plate 112.

A radiation projection device 126, 128 is arranged on the rotor 124. The radiation projection device 126, 128 has a radiation source 126 which is designed to emit radiation quanta and a detector 128 which is designed for detection of radiation quanta. The radiation quanta 127 can pass from the radiation source 126 to the region to be imaged and, following an interaction with the region to be imaged, strike the detector 128. In this way, a projection profile of the region to be imaged can be detected.

At least one projection profile respectively can be detected for different arrangements of the radiation source 126 and the detector in respect of the region of the object to be imaged by rotation of the radiation projection device 126, 128 about the image recording region. A plurality of projection profiles can form a projection data set. A medical image, in particular a tomographic medical image, of the region to be imaged can be reconstructed on the basis of a projection data set by the image reconstruction unit 136.

The imaging device 100 has a control device (controller) 130 for controlling the imaging device 100. The imaging device 100 also has an input unit (interface or input device) 138 for inputting control information, for example, imaging parameters, and examination parameters and an output unit (interface or display) 139 for outputting control information and images, in particular a medical image with a segmentation outcome obtained by the method according to one aspect of the invention.

The control device 130 can be, for example, a computer and/or a data processing system. The control device 130 includes the computer-readable medium 132, the processor 134, the data processing unit 135 and the image reconstruction unit 136.

Targeting the radiation source 126 on an area of interest such as an abnormality reduces the radiation quanta delivered to the patient 113. In order to do this, the control device 130 is required to know the position and body shape of the patient 113. Typically, the control device 130 uses a crude, yet body representation, based on body data obtained from a variety of sources. This crude body representation can, for example, be formed of a number of cylinders, such as a large cylinder for the body, and four smaller cylinders for the limbs of the patient, each of these cylinders may be adjusted by parameters such as patient age, height and weight.

In other examples, the crude body representation is estimated based on a statistical body shape model, such as a shape completion and animation of people model, which is a data-driven human shape model based on SCAPE. However, such models do not accurately represent the clinical setup. For example, while such models are based on a human body in a standing pose, this is not the case for patients, such as the patient 113 shown in FIG. 1, when they are positioned in the imaging apparatus. As is illustrated by the patient 113 in FIG. 1, a patient is generally laying down with his or her back flat against the table, whereas the models generally used represent standing body representations, where the back is somewhat curved. Whilst some adjustments may be made to simulate skeletal changes and fat tissue deformations, they are error-prone due to inherited uncertainty in these simulations.

Given the accuracy required during imaging, in particular, to target radiation quanta, or when undertaking other functions in relation to the imaging of patients described above, it is desirable to ensure that the most accurate body representation is used when targeting and setting other system parameters such as the frequency of pulses in MRI. This facilitates image acquisition and mitigates unnecessary side effects. The body representation may be a representation of a human or animal body. There is a large amount of high-quality medical imaging data available which is associated with many patient characteristics. Importantly, the medical imaging data also represents patients in the required position thereby increasing the accuracy of a body representation generated from it. However, such medical imaging data is partial, representing only portions/sections of the body. Therefore, on its own cannot be used to generate a mesh representing a full-body or partial-body representation as required. Furthermore, given that the data represents a portion of the body, a point cloud representation, given its unstructured nature, would be undesirable since it has an undefined topology and the associated post-processing would be complex. Similarly, given the high resolution of such data to generate a representation using voxels and/or a grid increase the complexity and processing power required.

To generate high quality and accurate body representations from such medical imaging data, in embodiments of the present invention machine learning techniques are used to estimate a patient body representation. This provides benefits of efficiency, accuracy and scalability. A machine learning system for representing a patient body may be trained using such high quality and representative medical imaging data which in turn can be used to estimate the body shape of a patient. The body representations which are adjusted based on the training of the machine learning system, and which may be inferred using the machine learning system may be models or templates of particular types of body. For example, the body representations may be associated with particular characteristics of the patient, such as body type, sex, weight, height. In some examples, the species of the patient may be one characteristic, that is, whether the patient is a human or animal. The estimate can then be used in treatment, such as to accurately target the radiation quanta.

Figure 2:
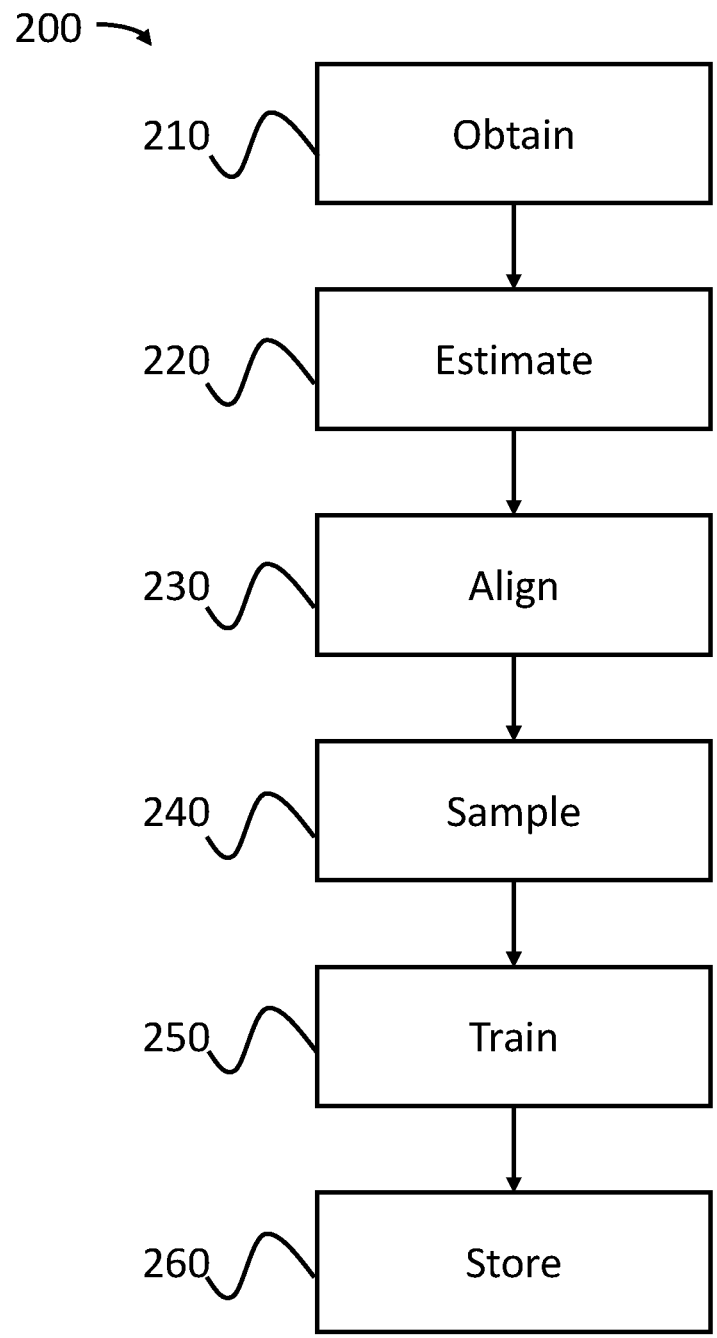
FIG. 2 is a flowchart showing a method of training a machine learning system for representing a patient body according to an example.

FIG. 2 is a flowchart showing a method 200 of training a machine learning system for representing a patient body, such as the machine learning system 440 described below with reference to FIG. 5. At block 210, a plurality of medical imaging data sets are obtained. The medical imaging data sets may be data captured by over time from a plurality of patients by one or more imaging apparatus using the same or different imaging modalities. Furthermore, the medical imaging data sets can represent different portions of a patient body. The medical imaging data sets may be collections of previously captured medical imaging data captured using different imaging modalities. For example, one set of medical imaging data could be CT imaging data of a particular patient with a particular type of body.

Furthermore, the medical imaging data may be grouped by patient characteristics, such as age, sex, weight, height such that multiple sets within the medical imaging data sets are grouped together and used when training machine learning systems in accordance with those patient characteristics. The data in the medical imaging data sets can be represented in a point coordinate and distance to the nearest surface format, which allows the use of different kinds of data irrespective of whether they represent a portion of a patient's body or the full patient's body irrespective of the original imaging modality. Furthermore, the medical imaging data sets may be obtained from a CT scanner, an MRI scanner, X-ray products, and/or ultrasound, however, it will be appreciated that other imaging apparatus and modalities may be used to gather such medical imaging data. The medical imaging data represents a plurality of different patient bodies, and as mentioned above may be representative of only a portion of the patient, such as the abdomen, head, or other body areas. Whilst it will be appreciated that the medical imaging data may be obtained from a single type of imaging apparatus, such as a CT scanner, it will also be appreciated that the medical imaging data can be obtained from multiple different types of imaging apparatus. The medical imaging data may be obtained from the storage of a control system, or obtained from a remote server via a network, such as the Internet. For example, the medical imaging data may be obtained from data management systems, such as EMR (electronic medical records), PACS (picture archiving and communication system), LIS (laboratory information system), RIS (radiology information system), and/or CVIS (cardiovascular information system).

Once the medical imaging data has been obtained, the method 200 progresses to block 220 where a plurality of landmarks are estimated in the stored medical imaging data. The landmarks may be associated with the portion of the body representation which the medical imaging data represents and may represent either internal or external landmark points. For example, the position of identifiers in the shape of organs may be estimated based on CT medical imaging data, however, it will be appreciated that other landmarks may be used based on the portion the medical imaging data represents. Such landmarks may be determined based on identifiable points of an anatomical object and the imaging modality used.

To detect the location of a first and second landmark point, a landmark detection machine learning algorithm may be applied to the medical imaging data. In some examples, the landmark detection machine learning algorithm is based on a deep reinforcement learning model that is trained to detect specific landmarks within the medical imaging data based on the imaging modality used. An artificial agent associated with the landmark detection machine learning algorithm is arranged to detect the landmarks points and may be trained via a deep reinforcement learning model. The artificial agent may be trained to learn the anatomical structures presented in medical imaging data and navigate towards the landmarks.

The deep reinforcement learning model used to train the artificial agent may be represented by the tuple $\{S, A, t, r\}$ where:

S is the state of the agent. The state of the agent may correspond to a portion of the medical imaging data centered at a point p. p represents the current location of the agent within the medical imaging data.

A is a set of actions to be undertaken by the agent. Since the agent is trained to locate landmarks within medical imaging data, A may represent different displacements along each Cartesian axis, x, and y, (and z, when the medical imaging data is three-dimensional medical imaging data) associated with the medical imaging data.

t is $S \times A \times S \rightarrow [0,1]$, which represents the stochastic transition function, describing the probability of arriving in a given state following a given action. For example, what is the likelihood of arriving at the landmark if the agent was to move in accordance with an action A.

r is the reward collected by the agent by interacting with the environment. r may be defined as:

$$r = ((p^c - p^{gt}))_2^2 - ((p^n - p^{gt}))_2^2$$

where $p^c$ represents the current location of the agent, $p^{gt}$ is a ground truth location of the landmark it is pursing, $p^n$ is the next location of the agent after it executes an action. As such, the closer the agent moves towards the target the higher the reward, and if the agent moves away from the target the reward has a negative value.

The agent may be represented by a fully convolutional neural network with a given number of layers. Given a particular path within the medical imaging data, the network may output six real values corresponding to a Q-value which represents the long-term return of an action. In this example, the Q-value represents an evaluation of the actions in the set of actions A. The maximum Q-value returned indicates the direction to move in the next step. Therefore, provided the agent has been trained on the correct anatomical structures, in order to collect the maximum rewards, the agent will always move closer to and then stop at the location of the target landmark. The above example is one example of how landmarks may be detected. It will be appreciated that other methods of detecting landmarks may be used including the use of other deep learning methods such as convolutional neural networks.

Once a plurality of landmarks have been estimated in the medical imaging data, the method 200 progresses to block 230, where the medical imaging data is aligned to a predefined pose based on the estimated landmarks. In some example, where there are multiple sets of medical imaging data representative of the same portion of the body, then the multiple representations may also be aligned such that a landmark in a first item of medical imaging data and a landmark in a second item of medical imaging data are aligned, before aligning both to the predefined pose. The predefined pose is a general representation of a body in the desired pose. The predefined pose may be a canonical pose, for example a pose that the patient is desired or required to adopt when being imaged. For example, in the case of CT imaging, the canonical pose may be a pose adopted by a patient lying on a table. Each of the estimated landmarks is aligned with corresponding landmarks on the predefined pose, so as to position each item of medical imaging data in the desired orientation and location. For example, the predefined pose may have landmarks representing a given feature of the person, such as the location of the eyes. Accordingly, landmarks representing the eyes in the medical imaging data may be identified and used to orient and position the medical imaging data, thereby aligning the medical imaging data to the predefined pose. Since each set of medical imaging data is representative of a portion of the desired representation, multiple sets of medical imaging data can be combined to represent the predefined pose.

Given that different medical imaging data sets may be used to build up a body representation of the patient, each medical imaging data set may not be in the same scale, and/or multiple medical imaging data sets may represent the same or substantially similar portion of the patient. Accordingly, in some examples it is desirable to apply an affine transformation to the medical imaging data. This involves rotating, scaling and/or translating the medical imaging data in relation to the predefined pose so that the landmarks align with predefined positions associated with the predefined pose. Furthermore, it may be necessary to scale the medical imaging data by normalizing the data such that the relevant medical imaging data sets can be aligned to a single body representation based on the patient characteristics, and/or in order to provide information associated with different types of patients.

Normalizing the medical imaging data includes determining a point which is farthest away from the center of the object represented in the medical imaging data and setting that distance to 1. The distance from the center to all other points may be represented based on that distance.

In light of this where there are multiple medical imaging data sets for a given portion of the body representation, the alignment of the medical imaging data sets may not be substantially perfect. In such an example, an averaging may be applied such that where medical imaging data sets having similar landmarks representing the same point on the predefined pose which are not aligned substantially perfectly, then the landmark positions may be averaged. Additionally, or alternatively, where the alignment of the landmarks within the medical imaging data sets is not substantially perfect, the closest fit/best match alignment may be chosen, with the aim of reducing the error between the predefined pose and the detected landmarks.

Following the alignment of the medical imaging data to the predefined pose, at block 240, points are sampled. Sampling points involves randomly selecting a plurality of points for comparison against the aligned medical data. Points may be represented as [x, y, z] and a signed distance from the point to the closest surface. The signed distance can represent the position of the point, such that a positive distance represents a point outside the surface boundary, and a negative distance represents a point inside the surface boundary. As such, the sign of the distance will change at the surface boundary. As mentioned above, given that multiple sets of medical imaging data are aligned to the predefined pose, points across the plurality of medical imaging data are able to be sampled, such as by obtaining three-dimensional coordinates of points which, based on the medical imaging data can be used to train a machine learning system.

Figure 5:
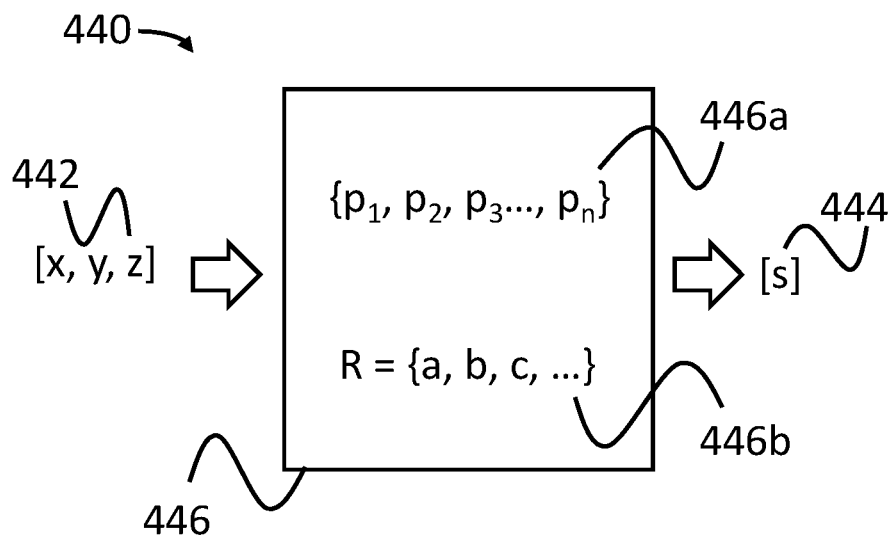
FIG. 5 is a representation of a machine learning system according to an example.

After sampling, a machine learning system 440, such as the machine learning system described below with reference to FIG. 5, is trained at block 250. The machine learning system is trained based on the sampled points and corresponding distances from each point to the closest body surface. The machine learning system may include, a deep neural network may be used which is trained using the point and corresponding distance to adjust the parameters and a body representation which is initialized in a random manner and adjusted throughout the training process. Instead of, or as well as, the neural network, it will be appreciated that the machine learning system may include any regression model, such as a random forest or any other appropriate algorithm or method. The machine learning system may be initialized with a random body representation, which along with the parameters of the machine learning system will be refined/configured based on the sample points and corresponding distances to the closest body surface. The random body representation may be an n-dimensional representation of the body. During training, the machine learning system is optimized by modifying one or more parameters and optimizing the random body representation based on the sampled points and associated distances. By refining the random body representation, the machine learning system is able to receive the sampled points and output a signed distance value to the closest surface. This signed distance value can be verified based on the known distance value associated with each sampled point. Based on the success or failure of the verification one or more parameters of the machine learning system may be adjusted accordingly. The parameters may be individual weightings and/or biases associated with a neuron of a neural network of the machine learning system, which along with the body representation are refined with the aim of providing a closer match between the measured distance value and the calculated distance value output by the machine learning system. This can be repeated for each sampled point, such that the body representation and the parameters of the machine learning system are refined. The trained machine learning system can then be used to determine a body representation based on received data, as will be described below in relation to FIG. 3.

At block 260, once the machine learning system has been trained, the parameters of the adjusted machine learning system are stored in storage (memory) associated with a system configured for training the machine learning system.

Figure 3:
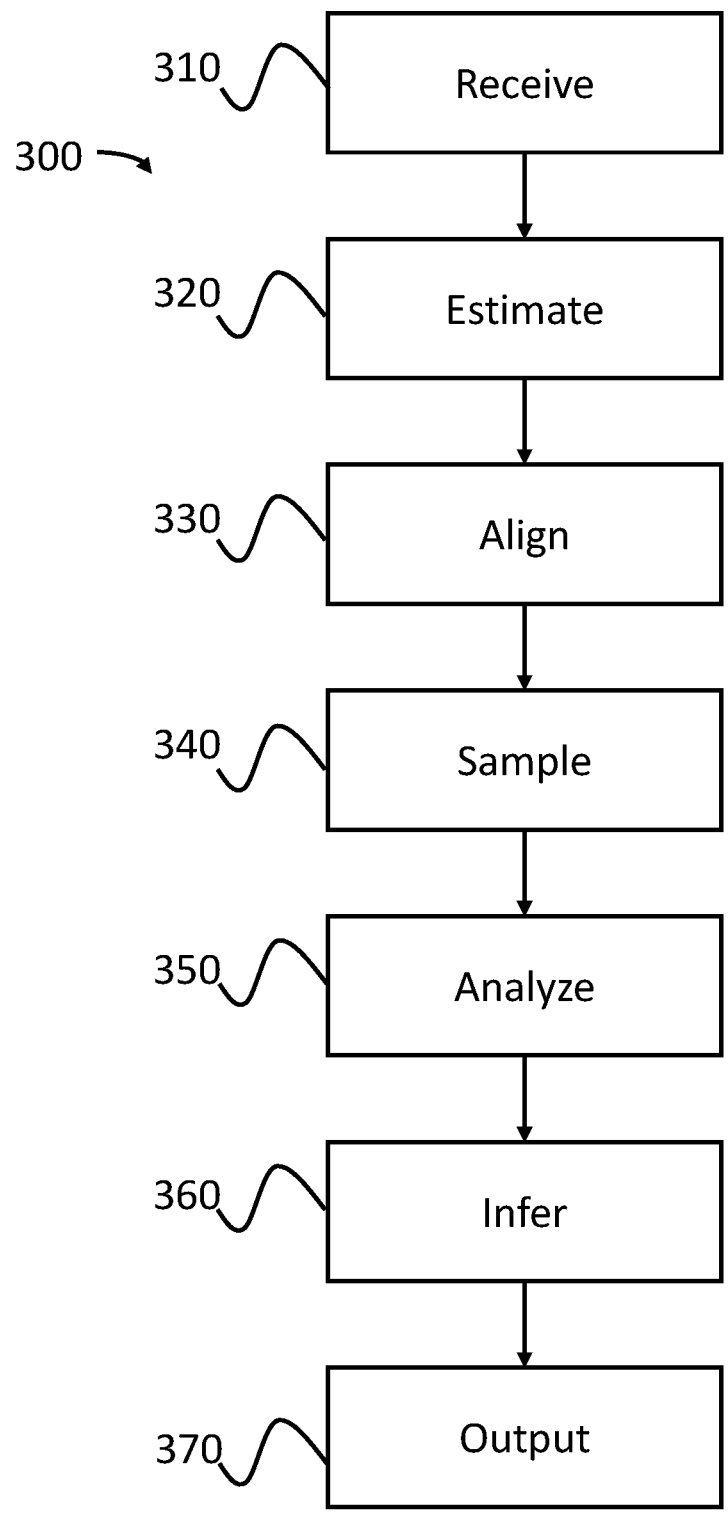
FIG. 3 is a flowchart showing a method of inferring a body representation according to an example.

FIG. 3 is a flowchart showing a method 300 of inferring a body representation according to an example. At block 310, image data is received. The image data may be medical data captured by a medical imaging apparatus such as a CT scanner, or may be depth data or point cloud data. It will be appreciated that the image data may be any three-dimensional data capable of indicating the position and shape of a patient and in some examples the internal anatomy of the patient. The image data in this example is captured using an imaging modality, via an imaging apparatus, such as a CT scanner, an MRI scanner, X-ray products, and/or ultrasound. However, it will be appreciated that other imaging apparatus and modalities may be used to gather such image data. The image data may be three-dimensional medical imaging data.

At block 320, the image data received is analyzed to estimate the location of one or more landmarks. Much like block 220 in method 200, described above, the estimation of landmarks may be undertaken using a machine learning algorithm, such as a deep reinforcement learning model. The landmarks may be internal landmarks, representing points within the patient's body, or they may be external landmarks representing points on a patient's body. The estimation of a plurality of these landmarks enables, at block 330, the alignment of the image data received from the imaging apparatus to the predefined pose used to generate the body representations described above in relation to FIG. 2. Furthermore, at block 340, a plurality of points are sampled on the image data to determine point coordinates and a signed distance to the closest body surface in the image data.

Once the plurality of points have been sampled, at block 350, an analysis is undertaken based on the sampled points and a trained machine learning system. The trained machine learning system may be the machine learning system generated using the method 200 described above in reference to FIG. 2, in which previously recorded medical imaging data is analyzed to determine a plurality of landmarks, and then aligned to a predefined pose. The machine learning system may be a machine learning system 440 described below with reference to FIG. 5. The method 200 of FIG. 2 is used to train a machine learning system based on sampled points and body representations that are refined during the training process. The analysis of the sampled points includes analyzing the sampled point coordinates calculated as part of the sampling process, determining signed distances and body representations using the trained machine learning system. A trained machine learning system may be a deep learning network, a random forest or regression model, although it will be appreciated that any machine learning system may be utilized. The trained machine learning system receives the sampled point coordinates and a randomized body representation, the machine learning representation uses the sampled points and randomized body representation to determine a signed distance and refines the body representation based on the signed distance output by the machine learning system. If a signed distance calculated based on the sampled point and medical imaging is substantially similar to a signed distance determined by the machine learning system, then the current body representation input to the machine learning algorithm is selected. Else, the body representation is adjusted, and the process is repeated until the output of the machine learning system is substantially similar to the determined signed distance. As such, this process may iterate until the best body representation is selected. Once the analysis has been undertaken, at block 360, an estimated body representation associated with the patient is inferred by, for example, selecting the body representation which results in the machine learning system outputting signed distances based on sampled points which closely align to calculated signed distances associated with the sampled points.

The inferred body representation may be output to a control device or an application on a control device, such as the control device 130 described above in relation to FIG. 1. The inferred body representation may be used as an input to one or more of a plurality of different implementations, including further machine learning systems arranged to determine a variety of information for use when imaging a patient. The further machine learning systems may be trained using the body representations generated according to the training process described above with reference to FIG. 2. For example, one application is the use of the inferred body representation within the imaging process to accurately target radiation quanta, since the body representation of the patient accurately reflects their characteristics, such as height, weight, and, in particular, position during the medical imaging process. The body representation is an n-dimensional vector which captures relevant information and can be used during the imaging process to guide the imaging process as described above. This improves the efficiency of any medical imaging which is subsequently undertaken. Other example applications include the automatic and accurate ISO-center computation in CT imaging; automatic scan-range estimation in CT, MR, and X-ray imaging; automatic patient registration in terms of height, weight and pose in CT, MR, and X-ray imaging; automatic and accurate specific absorption rate parameter estimation in MR imaging; automatic and accurate radiation dose computations in CT and X-ray imaging; and pre-operative versus intra-operative data registrations for augmented/virtual reality applications.

In further examples, the image data obtained in block 310 may be fed back into method 200 of FIG. 2, to further refine the machine learning system.

Figure 4:
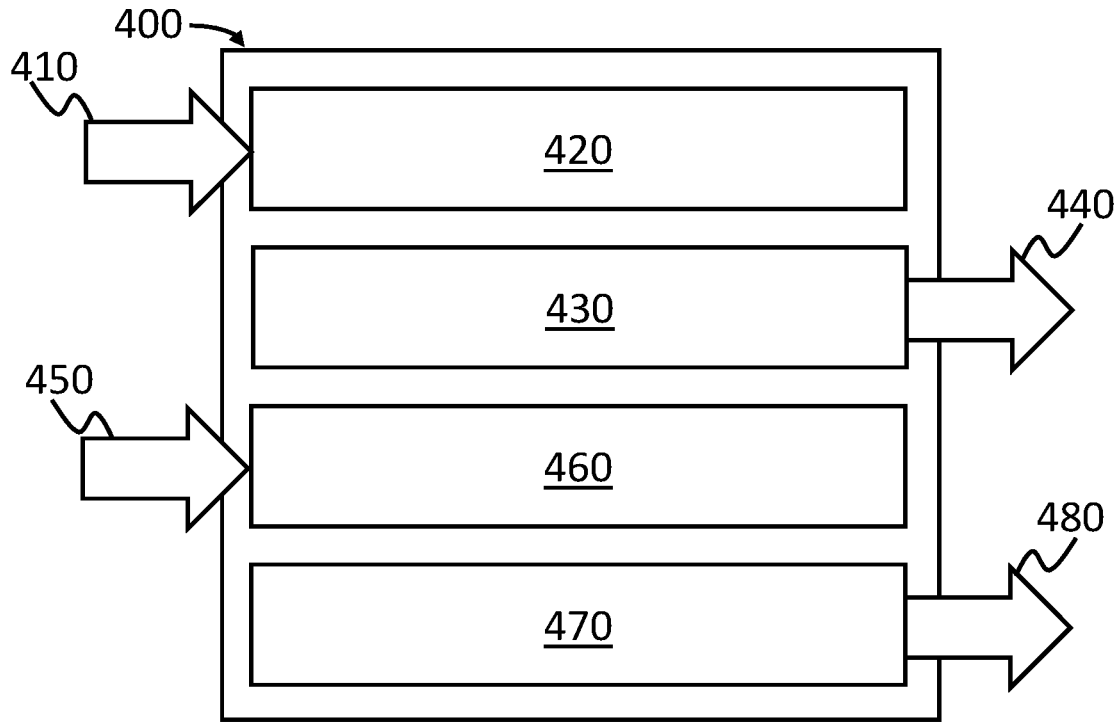
FIG. 4 is a schematic representation of an apparatus according to an example.

FIG. 4 is a schematic representation of an apparatus 400 according to an example. The apparatus 400 may form part of a system as will be described below in relation to FIG. 6 and is capable of implementing method 200 and method 300 described above in FIGS. 2 and 3 respectively.

The apparatus 400 is arranged to receive stored medical imaging data 410, the stored medical imaging data 410, as described above is a plurality of sets of medical imaging data previously captured and representing different types of patient. The stored medical imaging data 410 may be categorized according to patient characteristics. The stored medical imaging data 410 is obtained by a training interface 420, which in some examples may be connected to the storage (not shown) storing the stored medical imaging data 410. The training interface 420 may be configured to communicate via wired or wireless connection to the storage which may be external to the apparatus 400.

The apparatus 400 also includes a training unit (processor or machine) 430 configured to train at least one machine learning system based on the stored medical imaging data 410 obtained via the training interface. The training unit 430 is configured to perform method 200 described above in relation to FIG. 2 and train at least one machine learning system 440. The trained machine learning system 440 may be stored in storage (not shown) which may be the same storage which is configured to store the stored medical imaging data 410.

In addition, the apparatus 400 is also configured to receive image data 450 captured using an imaging modality. The imaging modality may be associated with an imaging apparatus (not shown) configured to capture the image data using the imaging modality. The image data 450 is received by an inference interface 460. Once received, the imaging data 450 is processed by the inference unit (processor) 470 configured to apply method 300 described above in relation to FIG. 3, and infer a body representation based on at least the captured imaging data 450 using the machine learning system 440 trained by the training unit 430.

Whilst the apparatus 400 described above and shown in FIG. 4 shows that both the training and inference are undertaken in the same apparatus, it will be appreciated that the training and inference may be undertaken by separate apparatus. Similarly, whilst the apparatus 400 shows a separate generation interface 420 and training interface 460, it will be appreciated that these may be a single interface configured to interact with storage (not shown) and the imaging apparatus (not shown).

FIG. 5 is a representation of a machine learning system 440 according to an example. The machine learning system 440 is capable of being trained to provide a body representation. As mentioned above with reference to method 200 of FIG. 2, the machine learning system 440 is trained based on a plurality of points 442 sampled from a plurality of medical imaging data sets. Each of the plurality of points 442 has a corresponding measured signed distance (not shown) which is based on the relationship of the point to the medical imaging data set (i.e. a ground truth value). For example, the measured signed distance may be the distance to the closest surface of an object represented in the medical imaging data set. The measured signed distance may be measured or calculated by, for example using one or more image processing methods, such as the fast marching method. Furthermore, whilst the example of FIG. 5 shows a point 442 including 3D cartesian coordinates, it will be appreciated that other coordinate systems may be used. The point 442 is passed to a trainable portion of the machine learning system 442 such as a deep neural network 446. It will be appreciated that the trainable portion may be any trainable machine learning algorithm such as a convolutional neural network, a random forest, or regression model.

The neural network 446, or other trainable portion, includes a plurality of parameters 446a which are adjustable during the training process. The neural network also includes a representation of the body 446b. The representation 446b may be an n-dimensional vector representative of a body shape/type. During the training process as described in relation to method 200 above, the representation 446b is randomly initialised, and as part of the training process is refined alongside the parameters 446a. The parameters may be individual weightings and/or biases associated with a neuron of a neural network of the machine learning system. Training the machine learning system 440 includes providing the plurality of points 442 and adjusting the parameters 446a and the representation 446b such that an estimated signed distance value 444 is output. If the estimated signed distance value output by the neural network or other trainable portion substantially corresponds to the measured signed distance (not shown) based on the medical imaging data sets, then the parameters 446a and representation 446b may be stored. The trained machine learning system 440 may then be used during the inference of a body representation as part of method 300 described above in relation to FIG. 3.

During the inference of a body representation as described above in relation to method 300 of FIG. 3, a plurality of sampled points 442 based on the received image data and associated measured distance values may be provided to the trained portion 446, which may be a trained neural network. Based on the trained parameters 446a of the trained portion 446, a body representation 446b may be inferred based on the plurality of points 442 provided as an input, and the signed distance expected 444 as an output. This is achieved by optimizing the values within the body representation 446b using the trained portion 446. The inferred body representation 446b may then be stored for use in further processing associated with a plurality of tasks, such as computing the SAR, estimating a patient weight, modulating radiation dose, or estimating scan parameters, as described above.

As mentioned above, the machine learning system may include a deep neural network which may be based on the deep neural network described in Section 4 of reference [1], section 3 of reference [2], or section 4 of reference [3].

Figure 6:
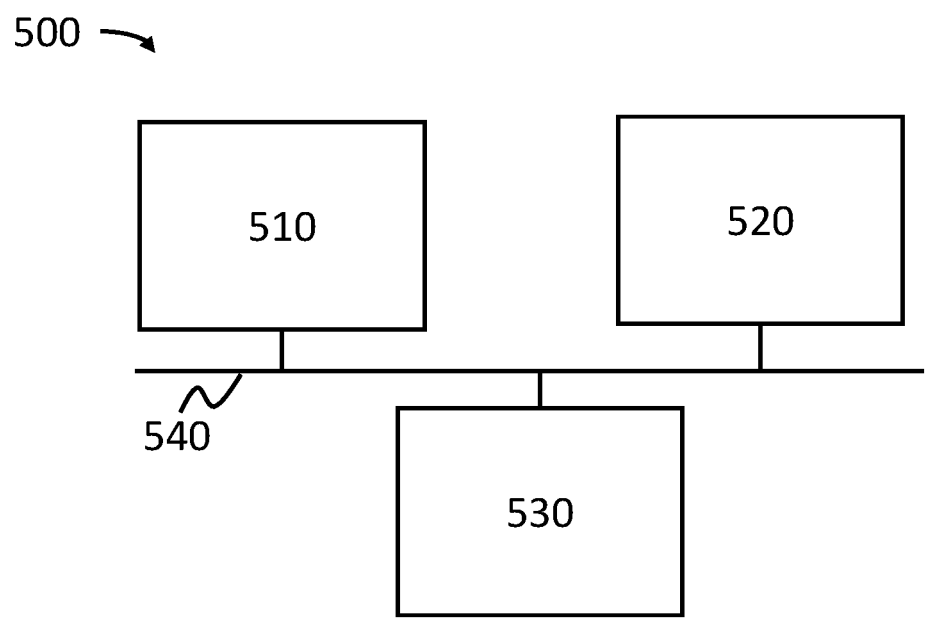
FIG. 6 is a schematic representation of a system according to an example.

FIG. 6 is a schematic representation of a system 500 according to an example. The system 500 includes at least one processor 510 configured to execute the methods 200, 300 described above in relation to FIGS. 2 and 3, and in some examples may be configured with the processing units described above in relation to FIG. 4. Accordingly, the processor 510 may include multiple processing units, such as image signal processors (ISP), graphics processing units (GPU), general-purpose central processing units (CPU), or neural processing units (NPU). The use of such processors may optimize the system 500 for making use of the described neural networks. This is because, as will be appreciated, such processors can make use of multi-thread processing and handle a large number of threads at the same time.

Furthermore, the processor 510 may exist alongside other components such as memory 520 used for storing instructions to enable the processor 510 to implement the methods 200, 300 described in relation to FIGS. 2 and 3 for training a machine learning system and inferring a body representation. The memory 520 is also configured to store medical imaging data used during the training of the machine learning system. The storage or memory 520 may also be configured to store instructions for the neural networks described in relation to blocks 220 and 320 for identifying landmarks within medical imaging data. Alternatively, the one or more neural networks, the instructions, and the stored medical imaging data may be supplied thereafter (e.g. in the form of a computer program product) by a computer-readable storage medium such as a compact disk (CD), a digital versatile disk (DVD), hard disk drive, solid-state drive, a flash memory device and the like. Alternatively, the one or more neural networks and the instructions may be downloaded onto the storage medium 430 via a data communication network (e.g. the Internet).

The system 500 also includes an imaging apparatus 530 configured to acquire the image data, such as CT imaging apparatus, MRI imaging apparatus, an x-ray imaging apparatus, an ultrasound probe, or a depth sensor. In some imaging apparatus, a scouting scan may be performed. The scouting scan is a relatively quick scan of the patient, and in some examples such as CT/X-ray imaging limits the exposure of the patient to low dose/low energy radiation. As such, the system 500 may include an image acquisition machine configured to obtain image data using the desired imaging modality.

The components 510, 520, 530 of the system 500 may be interconnected with other components of the system 500, for example using a system bus, although it will be appreciated that one component may be directly connected to one another component such that the output of a first component is connected directly to the input of a second component in a pipeline. This allows data to be transferred between the various components efficiently without the need to first store the output of the first component.

Whilst the invention has been illustrated and described in detail in the context of specific examples, the invention is not limited to the disclosed examples. Other variations can be deduced by those skilled in the art without leaving the scope of protection of the claimed invention.

In summary, disclosed is a method, apparatus, system and computer-readable storage medium for training a machine learning system for representing a patient body, including obtaining a plurality stored medical imaging data wherein a first one of the plurality of stored medical imaging data sets represents a different part of the patient body than a second one of the plurality of stored medical imaging data sets, and estimating a plurality of landmarks in the stored medical imaging data. Each of the stored medical imaging data is aligned to a predefined pose using the plurality of landmarks, and a plurality of points in the stored medical imaging data are sampled. The sampled points are then used to train a machine learning system by configuring the parameters if the machine learning system which are then stored.

Also disclosed is a method, apparatus, system and computer-readable storage medium for inferring a body representation including receiving image data captured using an imaging modality representing at least a portion of a patient and estimating a plurality of landmarks in the image data. The medical imaging data is aligned to a predefined pose using the plurality of landmarks, and a plurality of points in the image data are sampled. The plurality of points are then analyzed using a trained machine learning system, the machine learning system being configured to represent a patient body, which in turn is used to infer the body representation. The inferred body representation is then output.

BIBLIOGRAPHY

[1] Park et al., "DeepSDF: Learning Continuous Signed Distance Functions for Shape Representations", arXiv.org, 2019.
[2] Mescheder et al., "Occupancy Networks: Learning 3D Reconstruction in Function Space", arXiv.org, 2019.
[3] Chen Z, Zhang H, "Learning Implicit Fields for Generative Shape Modeling", arXiv.org, 2019.

The invention claimed is:

1. A computer-implemented method for training a machine learning system for representing a patient body, the computer-implemented method comprising:
    obtaining a plurality of stored medical imaging data sets each representing at least a part of a respective patient, wherein a first one of the plurality of stored medical imaging data sets represents a different part of the patient body than a second one of the plurality of stored medical imaging data sets;
    estimating a plurality of landmarks in the stored medical imaging data sets;
    aligning each of the stored medical imaging data set to a predefined pose using the plurality of landmarks, the aligning resulting in a plurality of aligned medical imaging data sets;
    sampling a plurality of points in the aligned medical imaging data sets;
    machine training the machine learning system based on at least the plurality of points to configure parameters of the machine learning system; and
    storing at least the configured parameters of the machine learning system.

2. The computer-implemented method according to claim 1, wherein the stored medical imaging data set is at least one of: computed tomography data; magnetic resonance imaging data; x-ray imaging data; or ultrasound imaging data.

3. The computer-implemented method according to claim 1, wherein sampling the plurality of points comprises for each of the plurality of points, determining a distance to a closest surface represented in the medical imaging data set.

4. The computer-implemented method according to claim 3, wherein training the machine learning system comprises adjusting at least one body representation, based on at least one of the plurality of points and corresponding distance to the closest surface.

5. The computer-implemented method according to claim 4, wherein the at least one body representation is an n-dimensional vector.

6. The computer-implemented method according to claim 1, wherein estimating the plurality of landmarks comprises applying at least one landmark detection algorithm to the stored medical imaging data set, the landmark detection algorithm being a machine learning algorithm trained to identify one or more landmarks of a body.

7. The computer-implemented method according to claim 1, wherein aligning the stored medical imaging data set, comprises:
    identifying at least one first medical data landmark in a first medical imaging data set;
    identifying at least one second medical data landmark in a second medical imaging data set, wherein the first medical data landmark and the second medical data landmark represent corresponding landmarks; and
    aligning the first medical imaging data set and the second medical imaging data set based on the first medical data landmark and the second medical data landmark.

8. The computer-implemented method according to claim 1, wherein the machine learning system comprises at least one neural network.

9. A computer-implemented method of inferring a body representation, the computer-implemented method comprising:
    receiving image data captured using an imaging modality representing at least a part of a patient;
    estimating a plurality of landmarks in the image data;
    aligning the image data to a predefined pose using the plurality of landmarks, the aligning resulting in aligned image data;
    sampling a plurality of points in the aligned image data;
    analyzing the plurality of points using a trained machine learning system, the trained machine learning system being configured to represent a patient body;
    inferring the body representation based on the analysis; and
    outputting the inferred body representation.

10. The computer-implemented method according to claim 9, wherein the image data is captured by an imaging apparatus, the image data being at least one of:
    computed tomography data; magnetic resonance imaging data; x-ray imaging data;
    ultrasound data;
    point cloud data; or depth data.

11. The computer-implemented method according to claim 9, wherein sampling the plurality of points comprises, for each of the plurality of points, determining a distance to a closest surface represented in the image data, thereby determining a plurality of distances.

12. The computer-implemented method according to claim 11, wherein inferring the body representation comprises iteratively providing a body representation and the plurality of points to a trained machine learning system, and comparing the respective outputs of the machine learning system with the plurality of distances associated with the plurality of points.

13. The computer-implemented method according to claim 12, further comprising adjusting the randomized body representation based on the comparison between the respective outputs and the plurality of distances associated with the plurality of points.

14. The computer-implemented method according to claim 13, wherein aligning the image data comprises:
    identifying at least one first data landmark in the received image data;
    identifying at least one second data landmark data associated with the predefined pose, wherein the first data landmark and the second data landmark represent corresponding landmarks; and
    aligning the received image data and the predefined pose based on the first data landmark and the second data landmark.

15. The computer-implemented method according to claim 9, wherein the body representation is an n-dimensional vector.

16. The computer-implemented method according to claim 9, wherein estimating the plurality of landmarks comprises applying at least one landmark detection algorithm to the medical imaging data, the landmark detection algorithm being a machine learning algorithm trained to identify one or more landmarks of a body.

17. The computer-implemented method according to claim 9, wherein aligning the image data comprises:
   identifying at least one first data landmark in the received image data;
   identifying at least one second data landmark data associated with the predefined pose, wherein the first data landmark and the second data landmark represent corresponding landmarks; and
   aligning the received image data and the predefined pose based on the first data landmark and the second data landmark.

18. A system for inferring a body representation, the system comprising:
   an imaging apparatus configured to capture image data;
   at least one processor configured to:
      estimate a plurality of landmarks in the image data;
      align the image data to a predefined pose using the plurality of landmarks, the alignment resulting in aligned image data;
      sample a plurality of points in the aligned image data;
      analyze the plurality of points using a trained machine learning system, the trained machine learning system being configured to represent a patient's entire body;
      infer the body representation based on the analysis; and
      output the inferred body representation.

19. The system according to claim 18, wherein the imaging apparatus comprises:
   a computed tomography system;
   a magnetic resonance imaging system;
   an x-ray imaging system; or
   an ultrasound system.

* * * * *